United States Patent [19]

Beer et al.

[11] Patent Number: 5,711,954
[45] Date of Patent: Jan. 27, 1998

[54] STABLE IMIDAZOLE ANTI-FUNGAL POWDER COMPOSITIONS

[75] Inventors: Don C. Beer, Cordova; Vijay B. Surpuriya, Germantown, both of Tenn.

[73] Assignee: Schering-Plough HealthCare Products, Inc., Memphis, Tenn.

[21] Appl. No.: 347,412

[22] PCT Filed: Jun. 7, 1993

[86] PCT No.: PCT/US93/05176

§ 371 Date: Mar. 7, 1995

§ 102(e) Date: Mar. 7, 1995

[87] PCT Pub. No.: WO93/25238

PCT Pub. Date: Dec. 23, 1993

Related U.S. Application Data

[63] Continuation-in-part of Ser. No. 894,896, Jun. 8, 1992, abandoned.

[51] Int. Cl.$^6$ .................................................... A01N 25/26
[52] U.S. Cl. ..................... 424/409; 424/405; 424/417; 424/420; 424/421; 514/401
[58] Field of Search .............................. 424/405, 409, 424/42 D, 42, 417, 420, 421; 514/901, 531, 73, 94, 119

[56] References Cited

U.S. PATENT DOCUMENTS

| | | | |
|---|---|---|---|
| 3,660,577 | 5/1972 | Buchel et al. | 424/273 |
| 4,457,938 | 7/1984 | von Bittera et al. | 424/273 R |
| 5,043,155 | 8/1991 | Pukhalski et al. | 424/78 |
| 5,262,150 | 11/1993 | Laugier et al. | 424/47 |

FOREIGN PATENT DOCUMENTS

| | | |
|---|---|---|
| 0 064 283 | 11/1982 | European Pat. Off. |
| 0058887 | 11/1982 | European Pat. Off. |
| 1586848 | 6/1970 | France. |
| 57-112315 A | 7/1982 | Japan. |
| 2137091 | 12/1984 | United Kingdom. |

OTHER PUBLICATIONS

Derwent 82–69438E, Jul. 1982, Abstract for Japan 57112315 A, below.
PDR—Mycelex p. 1410 Tablets of Clotrimazole, 1985.
Article from the New York Times, Wednesday, Nov. 27, 1991, "Personal Health–How old is that drug in your medicine cabinet?" by Jane E. Brody.
Product Description (two pages) and Material Safety Data Sheet (6 pages) for Supra–A SMM talc, Cyprus Industrial Minerals Company, Englewood, Colorado, Jan. 1992.

*Primary Examiner*—Neil S. Levy
*Attorney, Agent, or Firm*—Joseph T. Majka

[57] ABSTRACT

A stable powder composition comprising an anti-fungal effective amount of an imidazole antifungal compound and talc coated with a hydrophobic coating is described. A method for stabilizing an imidazole antifungal compound in a talc composition is also described which comprises either using talc coated with a hydrophobic coating or coating talc with a hydrophobic coating, prior to adding the imidazole antifungal compound to the talc.

13 Claims, No Drawings

STABLE IMIDAZOLE ANTI-FUNGAL POWDER COMPOSITIONS

The present application is the United States national application corresponding to International Application No. PCT/US 93/05176, filed Jun. 7, 1993 and designating the United States, which PCT application is in turn a continuation-in-part of U.S. application Ser. No. 07/894,896, filed Jun. 8, 1992, now abandoned, the benefit of which applications are claimed pursuant to the provisions of 35 U.S.C. 120,363 and 365 (C).

BACKGROUND

Imidazole compounds make up an important class of antifungal compounds used to treat yeast and fungal infections. Talc has a history of consumer acceptance and is used to provide a dry and smooth feel to topical powder formulations. Talc-based powder formulations of certain imidazole compounds (ie. clotrimazole) were found to show significant degradation of the active ingredient during storage under accelerated shelf-life conditions. Deteriorating stability is important to consumers since such drugs may deliver a weaker dose than was prescribed (Jane E. Brody, The New York Times, Wednesday, Nov. 27, 1991—Personal Health: How old is that drug in your medicine cabinet?). European Patent application 0 064 283 A2 teaches that talc compositions containing sulfur-containing imidazole antimicrobial compounds can be stabilized by adding a stabilizing amount of a basic metal salt of an inorganic or organic acid. However, the results of our study indicate that the addition of hydrophilic, or water loving compounds, such as basic metal salts to talc mixtures containing non-sulfur containing imidazole compounds such as clotrimazole, did little to control its decomposition. Accordingly, a different approach was needed to improve the stabilization of clotrimazole and other non-sulfur containing imidazole compounds.

SUMMARY OF THE INVENTION

We have discovered that the stability of imidazole antifungal compounds in powder compositions containing talc can be substantially enhanced by providing to the talc a hydrophobic coating which is repellant to water.

Accordingly, the present invention is directed towards a stable powder composition comprising:

a) an effective amount of an imidazole antifungal compound selected from clotrimazole, miconazole, terconazole, econazole, isoconazole, tioconazole, sulconazole, butoconazole, oxiconazole, bifonazole, fenticonazole, omoconazole, parconazole, ketoconazole, metronidazole, itraconazole or mixtures thereof; and b) talc coated with a hydrophobic coating in an amount from 0.5 to 5% by weight of the powder composition.

Preferably the hydrophobic coating is wax, tetrafluorethylene fluorocarbon polymers, silicone or mixtures thereof.

The present invention is also directed toward a method for stabilizing an imidazole antifungal compound in a talc composition, comprising either preparing a mixture of talc coated with a hydrophobic coating in an amount from 0.5 to 5% by weight of the powder composition, with an imidazole antifungal compound, or coating talc with a hydrophobic coating in an amount from 0.5 to 5% by weight of the powder composition, followed by preparing a mixture of the imidazole antifungal compound with the coated talc.

The present invention has the advantage of providing pharmaceutical powder compositions in which the stability of the imidazole active ingredient is improved under accelerated and normal shelf-life conditions. A second advantage of the present invention is that it provides talc powders coated with a hydrophobic coating that still maintain the smooth and free flowing properties characteristic of uncoated talc.

DETAILED DESCRIPTION OF THE INVENTION

The active ingredients (ie. imidazole antifungal compounds) are known in the art, as taught in U.S. Pat. No. 5,041,278. Such compounds can be employed in the powder compositions in amounts ranging from about 5 to about 0.5 percent by weight of the powder composition, preferably from about two to about one percent by weight, more preferably about one percent. Mixtures of various imidazole antifungal compounds can be employed, generally in ratios ranging from four to one parts of a first imidazole antifungal compound (ie. clotrimazole) to one part of a second imidazole antifungal compound (ie. miconazole), generally in about equal parts.

The term hydrophobic refers to the property of a substance that, upon its coating of uncoated talc, causes the surface of the coated talc to become substantially repellant to water.

Talc, also known as talcum, soapstone, steatite or french chalk, is a grayish-white, very fine, odorless, crystalline powder available from numerous manufacturers and fine chemical supply houses. Chemically, talc is a finely divided native hydrous magnesium silicate. One of ordinary skill in the art will recognize that talc from different sources or even the same source can vary greatly with regard to morphology and surface properties, such as surface charge and surface area. The present invention has the advantage of providing imidazole powder compositions with consistent stability over a variety of talc sources.

Hydrophobic coatings which can modify the surface-active properties of talc and retard degradation of the imidazole compounds include waxes, tetrafluorethylene fluorocarbon polymers or silicone. The hydrophobic coatings are believed to minimize surface interactions of the imidazole antifungal compound and the talc by causing the surface of the talc to become more inert, ie. by surface modification.

Suitable waxes include natural waxes such as animal (beeswax, lanolin, shellac wax, Chinese insect wax), vegetable (carnauba, candelilla, bayberry, sugar cane) or mineral (fossil or earth waxes such as ozokertie, ceresin or montan or petroleum waxes such as paraffin, microcrystalline, slack or scale wax). Other suitable waxes include synthetic waxes, such as ethylenic polymers and polyol ether-esters ("Carbowax," sorbitol), such as chlorinated naphthalenes ("Halowax") and such as the hydrocarbon type waxes via Fischer-Tropsch synthesis. Preferably the wax is an ethanolamide of stearic acid.

Tetrafluoroethylene (TFE) fluorocarbon polymers, also known as Teflon® polymers can also be employed as a suitable hydrophobic coating.

Silicones represent any of a large group of siloxane polymers based on a structure consisting of alternate silicon and oxygen atoms with various organic radicals attached to the silicon, as described in G. Hawley, The Condensed Chemical Dictionary, 10th Edition, Van Nostrand Reinhold Company, New York, N.Y., 1135 pages.

The amount of hydrophobic coating present on the talc should be sufficient to minimize decomposition of the imidazole antifungal compound. Based upon an accelerated stability test of one month at 50° C. or three months at 37° C., this amount should be about 2% or less. Generally, the amount of hydrophobic coating in the powder composition can range from about 0.5 to about 5 percent (%) by weight, more preferably from about 0.5 to about 2%, most preferably about 1%.

Other diluents, such as starch, can be added to the powder composition to absorb moisture. Such diluents can be employed in amounts ranging from about one to about 50% by weight of the powder composition, preferably from about 5 to about 20% by weight, more preferably from about 10 to about 20% by weight of the composition.

The uncoated talc can be coated with a hydrophobic coating by dry blending at elevated temperatures. Alternatively, the uncoated talc can be coated with the hydrophobic coating by dissolving the hydrophobic coating in a suitable solvent such as an alcohol, ether, chlorinated hydrocarbon, alkane, mixtures thereof and the like, spraying the solvent containing the hydrophobic coating onto the uncoated talc and removing the organic solvent by conventional procedures such as evaporation, heating, distillation and the like to give talc coated with a hydrophobic coating. The talc coated with the hydrophobic coating can then be dry blended or sprayed with the imidazole antifungal compound to give the desired powder composition. A diluent such as starch can be added to the powder composition by dry blending the diluent with the powder composition. Alternatively, the starch and the imidazole antifungal compound can be mixed together and the subsequent mixture can be dry blended with the talc coated with a hydrophobic coating to give the desired powder composition. The powder compositions of the present invention can be prepared in any inert mixing vessel made of suitably inert materials such as glass or stainless steel.

Alternatively, commercially available talc coated with a hydrophobic coating but which does not contain any of the imidazole active ingredients can be used. One preferred coated hydrophobic talc is Supra-A SMM of Cyprus Industrial Minerals Company, Englewood, Colo. Supra-A SMM is 200 mesh platy Italian talc coated with 1% Monamid S™. Monamid S™ contains stearamide monoethanolamine (MEA), a hydrophobic coating. The talc in this product has a typical particle size which is about 70 microns diameter to about 0.4 microns, with a median particle size of about 15 microns diameter.

The following example serves to illustrate some of the powder compositions and the manner by which they can be practised, but as such, should not be construed as limitations upon the overall scope of the same.

EXAMPLE 1

Effect of Talc Coated with a Hydrophobic Coating on the Stability of Clotrimazole

| Talc Supra A SMM | 99.0% |
|---|---|
| Clotrimazole | 1.0% |

Mix clotrimazole with the same volume of talc and pass the mixture through a 60 mesh sieve. Mix this mix with the remaining talc and pass it through a 30 mesh sieve. Mix again. Test for stability by exposing the talc mixture to a temperature of 50° C. for one month and analyze for clotrimazole using a validated method using high pressure chromatography (HPLC). Results are presented in Table 1.

EXAMPLE 2

Effect of Talc Coated with a Hydrophobic Coating with an Added Starch Diluent on the Stability of Clotrimazole

| Talc Supra A SMM | 89.0% |
|---|---|
| Starch | 10.0% |
| Clotrimazole | 1.0% |

Mix clotrimazole and starch and pass the mixture through a 60 mesh sieve. Mix this mixture with talc and pass it through a 30 mesh sieve. Mix again. Test as in Example 1. Results are presented in Table 1.

TABLE I

| TREATMENT | LOSS OF CLOTRIMAZOLE |
|---|---|
| Uncoated talc | 7.2% |
| Wax coated talc | 1.4% |
| Wax coated talc + 10% Starch | 0.8% |

The data from Table 1 indicate the surprising and unexpected results that clotrimazole is significantly more stable in powder compositions formulated with wax coated talc, or with wax coated talc plus starch, compared to talc having no coating (ie. uncoated).

We claim:

1. A dry, free flowing, stabilized powder composition comprising:
   a) an imidazole antifungal compound selected from clotrimazole, miconazole, terconazole, econazole, isoconazole, tioconazole, sulconazole, butoconazole, oxiconazole, bifonazole, fenticonazole, omoconazole, parconazole, ketoconazole, metronidazole, itraconazole or mixtures thereof; and
   b) talc coated with a hydrophobic coating, wherein the amount of hydrophobic coating in the powder composition can range from about 0.5 to about 5% by weight of the powder composition, wherein said powder composition is obtained by either:
      i) mixed talc coated with the hydrophobic coating and the imidazole antifungal compound; or
      ii) coating talc with the hydrophobic coating, followed by preparing a mixture of the imidazole antifungal compound with the coated talc.

2. The composition according to claim 1 wherein the hydrophobic coating is an amount from about 0.5 to about 2% by weight of the powder composition.

3. The composition according to claim 1 wherein the hydrophobic coating is wax, tetrafluorethylene fluorocarbon polymers, silicone or mixtures thereof.

4. The composition according to claim 3 wherein the hydrophobic coating is wax.

5. The composition according to claim 4 wherein the waxy hydrophobic coating is stearamide monoethanolamine.

6. The composition according to claim 3 wherein the hydrophobic coating is wax in an amount from 0.5 to 2% by weight of the composition and the imidazole antifungal compound is clotrimazole.

7. The composition according to claim 1 further comprising a starch diluent.

8. The composition according to claim 7 wherein the amount of starch in the composition ranges from 5 to 20% by weight of the composition.

9. A method for stabilizing an imidazole antifungal compound in a dry, free-flowing powder composition, comprising either:

i) mixing talc coated with a hydrophobic coating wherein the amount of hydrophobic coating in the powder composition can range from about 0.5 to 5% by weight of the powder composition and an imidazole antifungal compound; or ii) coating talc with a hydrophobic coating in an amount from about 0.5 to 5% by weight of the powder composition, followed by preparing a mixture of the imidazole antifungal compound with the coated talc.

10. The method according to claim 9 wherein the imidazole antifungal compound is clotrimazole, miconazole, terconazole, econazole, isoconazole, tioconazole, sulconazole, butoconazole, oxiconazole, bifonazole, fenticonazole, omoconazole, parconazole, ketoconazole, metronidazole, itraconizole or mixtures thereof.

11. The method according to claim 10 wherein the hydrophobic coating is wax.

12. The method according to claim 10 wherein the hydrophobic coating is wax in an amount from 0.5 to 2% by weight of the composition.

13. The method according to claim 10 wherein the imidazole antifungal compound is clotrimazole.

\* \* \* \* \*